United States Patent [19]

Poncelet et al.

[11] Patent Number: 5,846,555
[45] Date of Patent: Dec. 8, 1998

[54] ORGANIC/INORGANIC GELS FOR DELIVERING CONTROLLED QUANTITIES OF ACTIVE COMPOUNDS IN AQUEOUS SOLUTIONS

[75] Inventors: Olivier Jean Christian Poncelet, Chalon Sur Saone; Danielle Marie Henriette Wettling, Chatenoy Le Royal; Jeannine Rigola, Chalton Sur Saone, all of France

[73] Assignee: Eastman Kodak Company, Rochester, N.Y.

[21] Appl. No.: 711,354

[22] Filed: Sep. 5, 1996

Related U.S. Application Data

[62] Division of Ser. No. 605,240, Feb. 9, 1996, Pat. No. 5,683,826.

[30] Foreign Application Priority Data

Mar. 27, 1995 [FR] France ................................. 95 03781

[51] Int. Cl.$^6$ ........................... A01N 25/08; A01N 25/26
[52] U.S. Cl. ........................ 424/421; 427/185; 514/770; 514/944; 514/965
[58] Field of Search ...................... 424/408, 421, 424/405, 409; 252/315.5; 514/944, 964, 770, 765, 965; 604/892.1

[56] References Cited

U.S. PATENT DOCUMENTS

| | | | |
|---|---|---|---|
| 1,853,397 | 4/1932 | Banks, III | 514/770 X |
| 3,760,805 | 9/1973 | Higuchi | 604/892.1 |
| 3,917,814 | 11/1975 | Hedges et al. | 424/421 X |
| 3,954,678 | 5/1976 | Marquisee | 252/62.53 |
| 4,010,233 | 3/1977 | Winter et al. | 264/63 |
| 4,708,834 | 11/1987 | Cohen et al. | 428/402.24 X |
| 4,764,382 | 8/1988 | Kydonieus et al. | 514/944 X |
| 4,995,897 | 2/1991 | Schramm et al. | 424/421 X |
| 5,180,585 | 1/1993 | Jacobson et al. | 424/405 X |
| 5,200,334 | 4/1993 | Dunn et al. | 435/182 |
| 5,229,124 | 7/1993 | Rei et al. | 424/409 |
| 5,427,935 | 6/1995 | Wang et al. | 424/418 X |
| 5,651,976 | 7/1997 | Price et al. | 424/421 X |
| 5,683,826 | 11/1997 | Poncelet et al. | 428/702 |

FOREIGN PATENT DOCUMENTS

| | | |
|---|---|---|
| 602 810 | 6/1994 | European Pat. Off. . |
| 1 590 573 | 6/1981 | United Kingdom . |
| 2 235 462 | 6/1992 | United Kingdom . |

*Primary Examiner*—Richard D. Lovering
*Attorney, Agent, or Firm*—John R. Everett

[57] ABSTRACT

The invention concerns a composite gel comprising an inorganic matrix containing a fibrous inorganic polymer in which an active organic compound is dispersed.

The invention also concerns a device comprising the gel and a process for delivering a controlled quantity of active organic compound in an aqueous solution.

The invention applies to the prevention of biological growth in aqueous solutions used domestically, agriculturally or industrially, in particular in the solutions used in photographic processing.

FIGURE of the drawing to be published with the Abstract: None

4 Claims, 1 Drawing Sheet

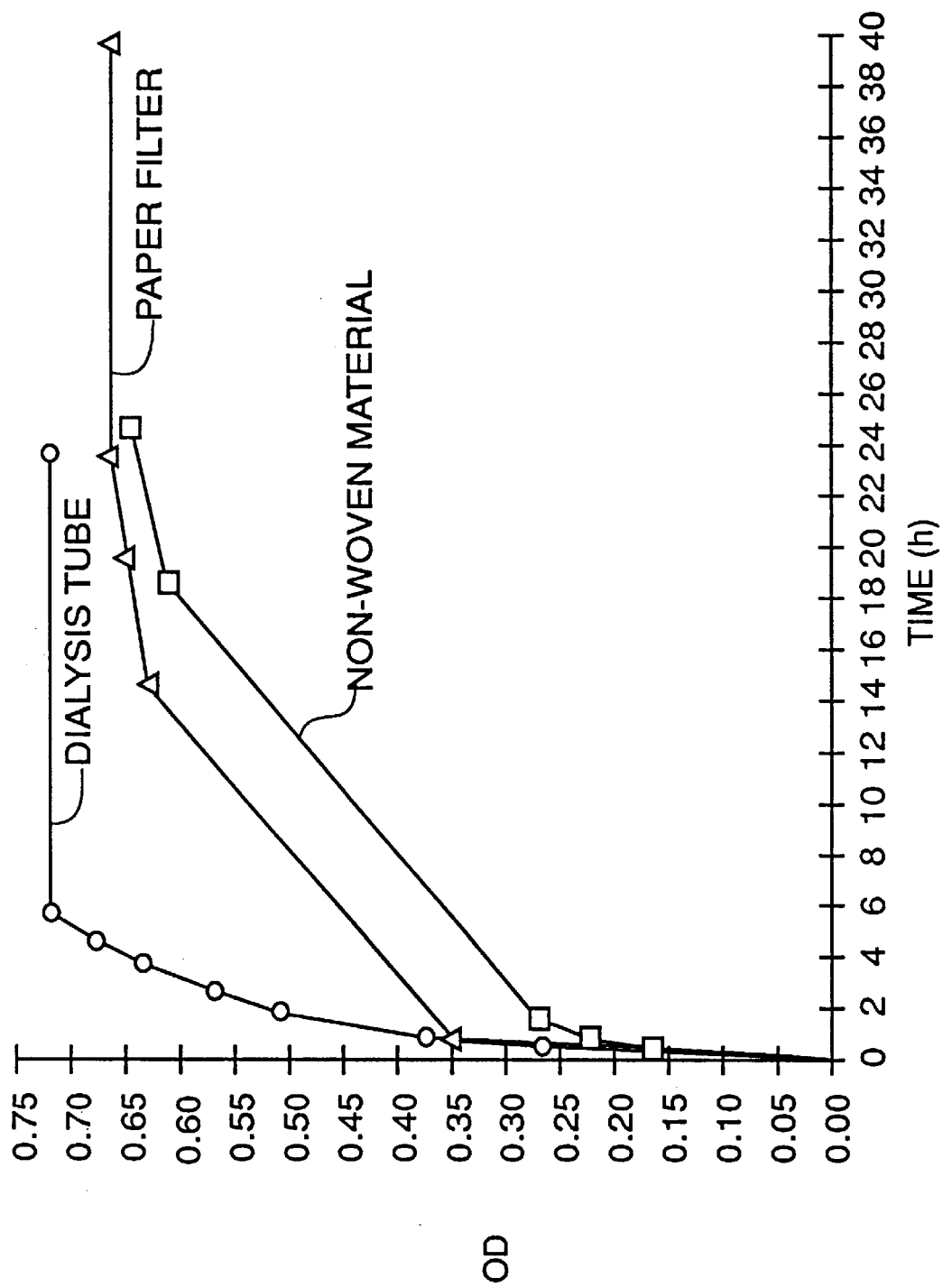

ORGANIC/INORGANIC GELS FOR DELIVERING CONTROLLED QUANTITIES OF ACTIVE COMPOUNDS IN AQUEOUS SOLUTIONS

This is a Divisional of application U.S. Ser. No. 08/605,240, filed 09 Feb. 1996, U.S. Pat. No. 5,683,826.

FIELD OF THE INVENTION

The invention concerns a gel comprising an inorganic matrix in which an active organic compound is dispersed. This gel enables a controlled quantity of active organic compound in an aqueous solution to be delivered. In particular, the invention concerns a gel comprising a fibrous inorganic polymer in which is dispersed a biocide or fungicide or any other organic compound for inhibiting biological growth. This gel can be used for limiting the growth of micro-organisms in aqueous solutions for domestic, agricultural or industrial use.

BACKGROUND OF THE INVENTION

In the photographic industry, biological growth occurs in the various photographic processing solutions, and in particular in the preliminary baths, rinsing solutions, bleaching baths and stabilising solutions. This problem is all the more critical since, for various reasons, such as the need to protect the environment or limited water resources, many photographic processes use small quantities of partly recycled water. The growth of micro-organisms, if not controlled, causes the formation of sludge and clogging of the equipment, deterioration of the processing bath and consequently a defective photographic image quality.

The use of biocides and fungicides for preventing or limiting biological growth in the processing solutions is normal practice. In order to give a safety margin, excess quantities, compared with the quantity which is just necessary, are used. In such case, the water discharged into the environment often contains large quantities of biocides or fungicides, which poses problems in treatment stations which use the action of micro-organisms in the treatment of effluents.

It would therefore be desirable to be able to deliver a controlled quantity of biocide or fungicide enabling biological growth in a photographic processing bath to be avoided or limited, without having the drawback of the presence of large quantities of bactericide or fungicide in the photographic effluents.

Patent application EP 602 810 describes a reinforced polyvinyl alcohol hydrogel containing uniformly dispersed and highly oriented crystalline regions that enhance the physical properties of the hydrogel. This material can be used for various applications, including for delivering controlled quantities of products, such as drugs, perfumes or biologically active compounds such as pesticides, fertilizers or herbicides.

The patent GB 2 235 462 describes a hydrogel composed of an organic polymer and an active compound. The hydrogel is swellable in water and is soluble in organic solvents. It can be used for delivering controlled quantities of biologically active compounds.

The patent GB 1 590 573 describes a gel comprising an organic polymer (I), an inorganic substance (II) and a biologically active compound (III). (I) and (II) may themselves be the active compounds. The active compound is a pesticide, a compound preventing the growth of plants of molluscs in water or an algicide. The structure of the gels and the rate at which the active compound is delivered are determined by the gelation conditions and the composition of the gel.

U.S. Pat. No. 5,229,124 describes solid solutions comprising a water-soluble organic polymer thermoplastic resin in which is dissolved a microbicide which is insoluble in water. These solutions enable the microbicide to be released slowly in the form of a dispersion in aqueous solutions.

The impregnation of mineral particles with biocides or fungicides is also known. U.S. Pat. No. 4,552,591 describes a composition intended to protect the polymers used in the oil field water treatment from bacterial attacks. This composition, comprising a liquid biocide adsorbed on mineral adsorbents, such as diatomaceous earth, is incorporated in the polymers liable to be in contact with aqueous fluids containing bacteria.

SUMMARY OF THE INVENTION

The present invention resolves the problem consisting of delivering controlled quantities of active organic compound in aqueous solutions using a composite gel, of a different nature from the gels of the prior art, comprising an inorganic matrix in which an active organic compound is dispersed, characterised in that the inorganic matrix comprises a fibrous inorganic polymer.

The composite gel according to the invention has the advantage of having a chemically inert inorganic matrix which does not react with the solution in which the gel is placed. In particular, the inorganic matrix does not react with the photographic processing solutions or with the films being processed; it therefore has no unfavourable effect on the sensitometry of the final images.

The invention also concerns a device for delivering a controlled quantity of active organic compound in an aqueous solution, consisting of means for containing the gel as defined above which allow the active organic compound to pass whilst retaining the inorganic matrix when the device is brought into contact with the aqueous solution.

The invention also concerns a process for preparing a composite gel comprising an active organic compound dispersed in a fibrous inorganic polymer, in which an ionic additive is added to an aqueous solution containing the inorganic polymer and the active organic compound, which brings about the gelation of the fibrous inorganic polymer and the trapping of the active organic compound.

Finally, the invention concerns a method for delivering a controlled quantity of active organic compound in an aqueous solution, in which a closed porous receptacle containing the gel defined above is introduced into an aqueous solution so that the active organic compound is delivered slowly into the aqueous solution and the inorganic matrix is retained in the receptacle.

BRIEF DESCRIPTION OF THE DRAWINGS

In the following description, reference will be made to FIG. 1, which shows the optical density corresponding to the quantity of active organic compound delivered as a function of time for various types of receptacle.

DETAILED DESCRIPTION OF THE INVENTION

The fibrous inorganic polymer according to the invention is preferably a crystallised polymeric aluminosilicate dissolved in water. A polymer of this type may be a product of tubular structure of the imogolite type prepared by the process described in U.S. Pat. No. 4,152,404, or a fibrous polymeric aluminosilicate of formula $Al_xSi_yO_z$ (x:y lying between 1 and 3 and z between 2 and 6), dissolved in water, obtained by the process described in Example 1 below.

According to the invention, it is also possible to use, as the inorganic matrix, a mixture comprising the fibrous inorganic polymer and chemically inert non-fibrous inorganic particles which do not react with the solution in which the gel is placed, such as particles of alumina, silica, aluminosilicate or hydrotalcites. A mixture useful in the present invention comprises at least 30% by weight of fibrous polymeric aluminosilicate, the remainder consisting of the non-fibrous inorganic particles.

The active organic compound used in the present invention is an organic compound, preferably hydrophilic, which is soluble in the aqueous solution in which it is delivered and which does not form covalent bonds with the fibrous inorganic polymer, otherwise it would remain trapped in the gel. In order to prevent biological growth, the active organic compound is a pesticide, an algicide, a fungicide or a bactericide.

Active organic compounds which can be used in photographic solutions are chosen, for example, from amongst the following bactericides and fungicides:

1) thiazole derivatives, such as the isothiazolones, for example 1,2-benzisothiazolin-3-one, 2-methyl-4-isothiazolin-3-one, 2-octyl-4-isothiazolin-3-one and 5-chloro-2-methyl-4-isothiazolin-3-one, 2) azole derivatives such as benzotriazoles or benzimidazoles, 3) agents of the sulfamide type, such as sulphanilamide, 4) organoarsenides such as 10-10'-oxybisphenoxyarsine, 5) benzoic acid, sorbic acid, 6) quaternary ammonium salts of benzalkonium, 7) nitro alcohols.

Preferred compounds are benzisothiazolones, for example 1,2-benzisothiazolin-3-one sold under the brand name Proxel® by Zeneca and isothiazolones, for example the mixture of 5-chloro-2-methyl-4-isothiazolin-3-one and 2-methyl-4-isothiazolin-3-one sold under the name of Kathon® by Rohm and Haas.

In order to obtain the composite gel comprising the fibrous inorganic polymer in which the active organic compound is dispersed, an ionic additive is generally added to an aqueous solution containing the fibrous inorganic polymer and the active organic compound in order to bring about homogenous gelation. The ionic additive must not react with the active organic compound and should preferably remain trapped in the gel when the gel is put in aqueous solution. If the aqueous solution in which the active organic compound is delivered is basic, it is possible to use basic ionic additives, such as the alkaline bases like ammonia solution and soda. If the aqueous solution is an acid solution, quaternary ammonium salts, phosphonates or long-chain sulphonates will, for example, be chosen.

A suitable device for containing the gel must allow the active organic compound to pass whilst retaining the inorganic matrix when the device is brought into contact with the aqueous solution. In practice, a porous material with a pore size of between 1 nm and 50 μm is used, such as for example chemically inert cellulose, in the form of a dialysis tube or a closed bag made from filter paper or non-woven material. The gel may be prepared directly in the porous receptacle.

The quantity of biocide required for a particular aqueous solution will depend on its composition, the volume of the solution to be treated (around 5 to 20 $m^3$ per week for photographic processing laboratories), the nature of the biocide, the conditions of use of this solution, the possible extent of the contamination by micro-organisms and the time during which it is desired to limit the growth of micro-organisms. The process according to the invention makes it possible to deliver the exactly necessary quantity of active organic compound over a given time, which may vary according to requirements from a few hours to several days. In practice, in order to obtain this quantity, an expert can act on two factors: the relative concentrations of the active organic compound and inorganic polymer in the gel (as will be seen in the examples) and on the quantity of gel put in the porous receptacle. Thus the formulation of the gel may be modified according to the speed at which the active organic compound is required to be delivered into the bath and according to the quantity of active organic compound to be delivered over a given time.

In practice, the concentration of biocide in the gel is approximately 10 times the concentration necessary to limit biological growth in the aqueous solution.

Useful concentrations of active organic compound and fibrous inorganic polymer are in a molar ratio of between 10:1 and 1:200.

EXAMPLES

Example 1

Preparation of fibrous polymeric aluminosilicate 16.7 mmoles of tetraethoxysilicon, $Si(OEt)_4$ was added to 1000 ml of pure water. The solution was stirred at room temperature for 1 hour, and then this solution was added to a solution of 31.2 mmoles of aluminium trichloride $AlCl_3$, $6H_2O$ in 1000 ml of pure water.

The solution was stirred vigorously for 20 minutes and then a solution of NaOH 1M was added to the colourless solution until a pH of 5.0 was obtained. A cloudy solution was obtained, which was stirred for one night. The pH was adjusted to 6.8 with NaOH 1M. A precipitate was obtained which was centrifuged for 20 minutes at 2000 rpm.

A white gel was collected which was solubilised with 5 ml of a 50:50 mixture of hydrochloric acid 1M and acetic acid 2M. The volume of the solution was made up to 1 liter. 250 ml of the solution obtained above was diluted in 550 ml of pure water and heated at a temperature of 95°–100° C. for two days in a stainless steel reactor with a diameter of 20 cm along with glass balls.

The parent solution obtained was kept at a temperature of 5° C. Every two days, 250 ml of the parent solution was added to the heated solution. When the temperature of the solution had dropped to approximately 20° C., a solution of ammonia $NH_4OH$ 1M was added slowly to adjust the pH to 8.0. A gel was obtained. The gel obtained was centrifuged for 15 minutes at 2000 rpm and the supernatant liquor was removed. The remaining gel was solubilised by the addition of a few drops of hydrochloric acid 12N and then dialysis was carried out with pure water for four days.

A thixotropic gel was obtained. Electron micrographs show that it has a uniform fibrous structure. Analysis of the compound shows that it has the formula $Al_2O_3,Si(OH)_4$.

Example 2 (invention)

A solution comprising 25 ml of fibrous polymeric aluminosilicate (0.375 mmole of $Al_2O_3,Si(OH)_4$) obtained in Example 1, 25 ml of a solution comprising 0.4 ml/l of Proxel® GXL biocide sold by Zeneca comprising, according to the specifications of the supplier, 20% by weight of an active compound from the benzisothiazolone group of formula:

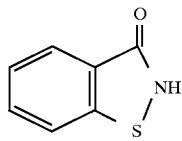

was poured into a Nadir® dialysis tube with a pore size of 5 nm.

1 ml of ammonia solution 1M was added. A viscous gel was obtained, containing 11.4 mg of Proxel® GLX, i.e. 2.28 mg ($1.5 \times 10^{-2}$ mmoles) of active compound.

The dialysis tube was immersed in 275 ml of an aqueous solution consisting of a preliminary photographic bath with a pH of 9.2 used in the Kodak MPTV ECP 2A® process and comprising borax, sodium sulphate and sodium carbonate.

In this example and in all the following examples, samples of the solution were taken at different times and the transmission spectrum and diffusion kinetics of the active compound were observed by means of a Perkin Elmer Lambda 15 spectrophotometer.

The concentrations of the active compound released in the solution are set out in Table I. The results take account of variations in volume of the solution due to the sampling.

It can be seen in Table I that the quantity of active compound released in the solution is greater during the first few hours and that saturation of the preliminary bath occurs after 4 h.

Example 3 (invention)

The procedure of the previous example was repeated, but increasing the concentration of active compound in the gel. To do this, a solution comprising 25 ml of fibrous polymeric aluminosilicate (0.375 mmoles of $Al_2O_3,Si(OH)_4$) obtained in Example 1, and 0.5 ml of pure Proxel® GXL, were poured into a dialysis tube of the Nadir® type with a pore size of 5 nm. A viscous gel was obtained, containing 570 mg of Proxel® GXL, ie 114 mg (0.755 mmoles) of active compound.

As before, the dialysis tube was immersed in 275 ml of an aqueous solution consisting of a preliminary photographic bath having a pH of 9.2. After 1½ hours, the solution was replaced with a fresh solution having the same composition.

This example shows that it is possible to obtain a gel with a high concentration of biocide (50 times more than in Example 2), which makes it possible in this way to increase the quantity of biocide released in the solution.

It can be seen that, if the gel is left in the solution several hours after saturation, and the solution is replaced with a fresh solution having an equal volume, the biocide is once again released and saturation occurs within the same period of time as with the solution initially present.

When the solution is renewed continuously, the active compound continues to be released until the active compound in the gel has completely disappeared.

The concentrations of the active compound released in the solution are set out in Table I.

Example 4 (invention)

The procedure of Example 2 was repeated, but replacing the Proxel® GLX with Kathon® LX sold by Rohm and Haas, which was an aqueous solution containing 13.7% by weight of an active compound from the isothiazolone group of formula:

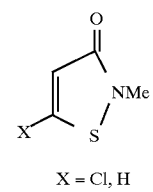

X = Cl, H in which the ratio Cl:H=1:3.

A solution comprising 258 ml of fibrous polymeric aluminosilicate (0.375 mmoles of $Al_2O_3,Si(OH)_4$) obtained in Example 1, 25 ml of a solution comprising 493 mg/l of Kathon® LX and 0.5 ml of ammonia solution 1M was poured into a Nadir® dialysis tube with a pore size of 5 nm. A viscous gel containing 12.32 mg of Kathon® LX was obtained, ie 1.69 mg ($7.23 \times 10^{-3}$ mmoles) of active compound.

As before, the dialysis tube was immersed in 275 ml of an aqueous solution consisting of a preliminary photographic bath with a pH of 9.2.

Saturation of the preliminary bath occured after 5 hours. The concentrations of active compound released in the solution are set out in Table I.

Example 5 (invention)

A solution comprising 25 ml of fibrous polymeric aluminosilicate (0.375 mmoles of $Al_2O_3,Si(OH)_4$) obtained in Example 1, 25 ml of a solution comprising 7.5 mg of Proxel® GLX and 1 ml of benzyltributylammonium 1M was poured into a Nadir® dialysis tube with a pore size of 5 nm. A viscous gel containing 7.5 mg of Proxel® GLX was obtained, i.e. 1.5 mg ($9.9 \times 10^{-3}$ mmoles) of active compound.

The dialysis tube was immersed in 275 ml of an aqueous solution with a pH of 6.

Saturation of the solution occured after 5 hours. If the solution is renewed completely, Proxel® GXL diffuses again.

The concentrations of active compound released in the solution are set out in Table I.

Example 6 (comparative)

The procedure of Example 2 was repeated, but replacing the Proxel® GLX with a benzisothiazolone of formula:

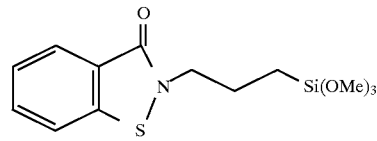

A solution comprising 25 ml of fibrous polymeric aluminosilicate (0.375 mmoles of $Al_2O_3,Si(OH)_4$), and 25 ml of a solution containing 0.4 mmoles/l of active compound and 1 ml of ammonia solution 1M was poured into a Nadir® dialysis tube with a pore size of 5 nm. A viscous gel containing 3.13 mg was obtained ($1 \times 10^{-2}$ mmoles of active compound).

As before, the dialysis tube was immersed in 275 ml of an aqueous solution consisting of a preliminary photographic bath with a pH of 9.2.

Saturation of the preliminary bath occured after 3 h since the biocide remains trapped in the inorganic polymer lattice.

The concentrations of active compound released in the solution are set out in Table I.

Example 7 (comparative)

A solution comprising 25 ml of fibrous polymeric aluminosilicate obtained in Example 1, 25 ml of a solution comprising 0.12 mmoles of an isothiazolone having a hydrophobic character of formula:

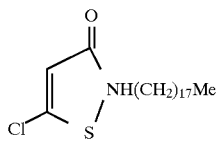

and 1 ml of ammonia solution 1M was poured into a Nadir® dialysis tube with a pore size of 5 nm.

As before, the dialysis tube was immersed in 275 ml of an aqueous solution consisting of a preliminary photographic bath with a pH of 9.2.

The biocide was not released in the solution. This is due to its hydrophobic nature.

The concentrations of active compound released in the solution are set out in Table I.

TABLE I

| | Concentration of active product in solution (mmole/l) | | | | | |
|---|---|---|---|---|---|---|
| Time | Ex. 2 | Ex. 3 | Ex. 4 | Ex. 5 | Ex. 6 | Ex. 7 |
| 0 h | 0 | 0 | 0 | 0 | 0 | 0 |
| 1 h | $2,01.10^{-2}$ | 1,83 | $1,92.10^{-2}$ | $0,64.10^{-2}$ | $1,4.10^{-2}$ | 0 |
| 3 h | — | 0,34* | — | $2,81.10^{-2}$ | $2,1.10^{-2}$ | 0 |
| 4 h | $4,56.10^{-2}$ | — | $2,1.10^{-2}$ | — | $2,1.10^{-2}$ | — |
| 22 h | $4,56.10^{-2}$ | 0,60 | $2,2.10^{-2}$ | $2,85.10^{-2}$ | — | — |
| 38 h | — | — | — | $0,16.10^{-2}$** | — | — |
| 15 days | — | — | $2,2.10^{-2}$ | — | — | — |

*The solution was entirely renewed after 1½ h.
**The solution was entirely renewed after 37 h.

Example 8 (invention)

Three identical gels were prepared in three different receptacles:

a Nadir® dialysis tube with a pore size of 5 nm, a bag made from filter paper with a pore size of 25 a bag made from non-woven material with a pore size of 10 μm, by mixing 50 ml of fibrous polymeric aluminosilicate (0.750 mmole of $Al_2O_3,Si(OH)_4$), 1 cc of a solution comprising 32.43 mg of Proxel® GLX and 2 cc of $NH_4O$ 1M. Each gel contained 6.5 mg ($4.3 \times 10^{-2}$ mmoles) of active compound.

Each receptacle was immersed in 275 ml of an aqueous solution with a pH of 9.2.

FIG. 1 gives the optical density corresponding to the quantity of active compound in the solution as a function of time. It can be seen that the diffusion is more rapid with the dialysis tube. The other two receptacles, which have substantially larger pore sizes, also make it possible to release controlled quantities of active compound.

We claim:

1. A device for delivering a controlled quantity of a biocide compound in an aqueous solution said device comprising means for containing a composite gel said composite gel comprising an inorganic matrix having a biocide compound dispersed therein, said inorganic matrix comprising an fibrous inorganic alumino silicate polymer, wherein said means allow the biocide compound to pass whilst retaining the inorganic matrix when the device is brought into contact with the aqueous solution.

2. Device according to claim 1, in which the means for containing the gel consist of a porous receptacle with a pore size between 1 nm and 50 μm.

3. Device according to claim 2, in which the porous receptacle is made from chemically inert cellulose.

4. Device according to claim 3, in which the means for containing the gel consist of a receptacle in the form of a dialysis tube or a closed bag made from filter paper or non-woven material.

* * * * *